United States Patent [19]

Fannin et al.

[11] Patent Number: 5,286,447
[45] Date of Patent: Feb. 15, 1994

[54] METHOD AND APPARATUS FOR CONTROLLING MICROBIAL GROWTH ON CONDENSATION COILS

[76] Inventors: Kerby F. Fannin, 7091 Bilby Rd., Jerome, Mich. 49249; David P. Chynoweth, 1034 NW. 61st Ter., Gainesville, Fla. 32605

[21] Appl. No.: 848,351

[22] Filed: Mar. 9, 1992

[51] Int. Cl.⁵ .................. A01N 25/00; A61L 2/00; A61L 9/00
[52] U.S. Cl. .................................. 422/28; 422/31; 422/116; 422/292; 55/279
[58] Field of Search ............... 422/28, 31, 120, 292, 422/116; 55/279; 62/78

[56] References Cited
U.S. PATENT DOCUMENTS

| | | | |
|---|---|---|---|
| 2,248,713 | 7/1941 | Locke | 422/121 |
| 2,628,083 | 2/1953 | Rense | 261/137 |
| 3,100,679 | 8/1963 | Kritzer | 422/121 |
| 3,421,836 | 1/1969 | Sundin et al. | 422/4 |
| 3,745,750 | 7/1973 | Arff | 422/24 X |
| 3,824,770 | 7/1974 | Eckstein | 422/3 X |
| 4,089,655 | 5/1978 | Razete | 422/120 |
| 4,990,313 | 2/1991 | Pacosz | 422/121 |

Primary Examiner—Robert J. Warden
Assistant Examiner—Krisanne M. Thornton
Attorney, Agent, or Firm—Beaman & Beaman

[57] ABSTRACT

The disclosure pertains to a method and apparatus for controlling microbial growth in air handling systems employing heat exchanging coils, water pans, or the like, exposed to moisture and subject to microbial contamination. Condensation apparatus located within a chamber defined in an air handling system is disinfected by temporarily interrupting normal air flow, sealing the chamber with respect to the air handling system, introducing an anti-microbial growth gaseous disinfectant into the chamber, removing the anti-microbial gas from the chamber after disinfecting the condensation apparatus and then restoring normal air flow through the chamber. The preferred anti-microbial gas is produced by using an ozone generator in conjunction with an auxiliary air flow system.

8 Claims, 2 Drawing Sheets

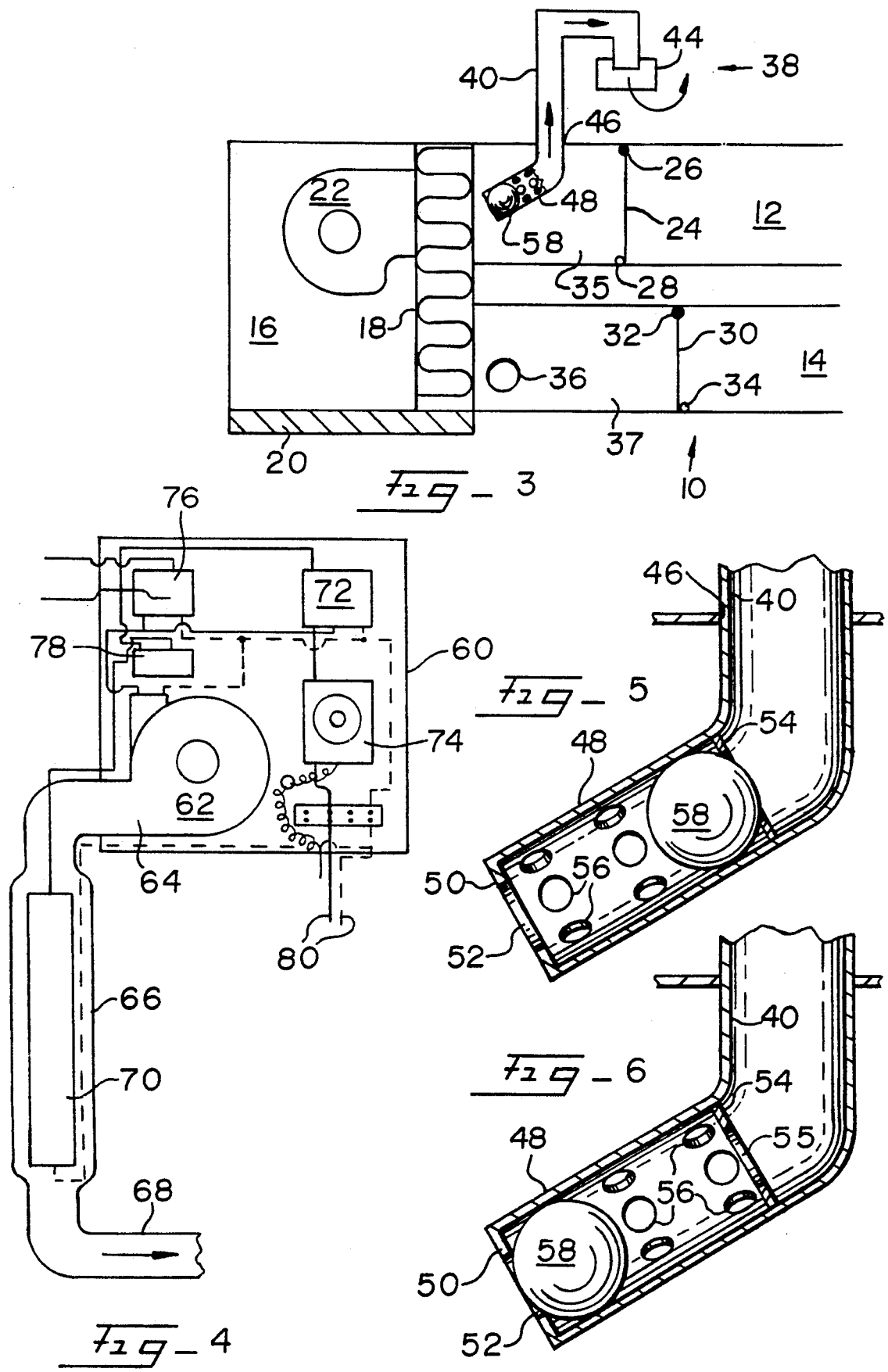

METHOD AND APPARATUS FOR CONTROLLING MICROBIAL GROWTH ON CONDENSATION COILS

BACKGROUND OF THE INVENTION

2. Field of the Invention

The invention pertains to systems for disinfecting condensation and moisture producing apparatus within air handling systems by the periodic exposure of the apparatus to an anti-microbial gas.

Apparatus producing condensation moisture within air handling systems is subject to contamination by the growth of microorganisms existing on the moist surfaces of the apparatus. Such situations occur in air conditioners, dehumidifiers and other air cooling systems wherein air passing through heat exchanging coils is rapidly cooled and the moisture within the air condenses on the coils and falls into a drip pan or other apparatus for removing moisture.

Microbial growth is common on surfaces where moisture, minerals and organic substances are present, and the growth of such microorganisms on condensing apparatus surfaces reduces the heat exchange efficiency and the overall performance of the apparatus. Additionally, microbial growth produces microorganisms which can become airborne during the operation of the air handling system, therein contaminating ducts and occupied spaces. Such contamination of indoor air has been widely documented, and is a major cause of illness among individuals within office buildings and the like having sealed windows wherein air circulation is only through central cooling and heating units. Contaminated air conditioning systems are known to cause "sick building syndrome", Legionnaire's disease, and hypersensitivity pneumonitis.

The problem of contamination of air handling systems such as those used in commercial buildings, private dwellings and vehicles is particularly acute in warm climate areas that require lengthy air conditioner operation without the opportunity to permit the moisture producing coils, drip pans, and the like to dry. In an effort to control contamination of air handling systems by microbial growth on condensation apparatus, various techniques have been employed. For instance, condensation collecting drip pans are designed to remove the majority of moisture as quickly as possible from the air handling system, but residual moisture will remain. Further, it is recommended that the condensation producing apparatus of air cooling equipment be regularly manually cleaned and disinfected. However, such regular and routine maintenance is often overlooked, and the use of conventional disinfecting techniques creates problems because of the dissipation of disinfectants into the air flowing through the system. Accordingly, air cooling systems are not usually regularly maintained and cleaned to avoid the microbial contamination which occurs and many occupants of buildings and vehicles having contaminated air systems are subject to allergies and illnesses difficult to trace and diagnose.

2.
Description of Related Art

The aforementioned problems with respect to microbial growth within air handling systems has long been recognized, but has not been effectively solved. It is known that the treatment of air within air handling systems by ultraviolet light frequencies can be helpful in controlling microbial growth, and apparatus for doing so is shown in U.S. Pat. Nos. 2,628,083 and 3,100,679. Likewise, an ultraviolet device is shown in U.S. Pat. No. 4,990,313 which would be suitable for use with domestic air cooling systems.

Ozone is known as a strong oxidant and an effective sterilant, and has been used to purify or sterilize refrigerated air, as shown in U.S. Pat. Nos. 2,248,713 and 3,421,836.

While the aforementioned patents propose to deal with the problem of the microbial contamination of air cooling systems, ultraviolet light devices have not proven effective to sufficiently sterilize the air and surfaces within air handling systems to control microbial growth, and while those systems using ozone more readily disinfect inaccessible surfaces than can be achieved with the ultraviolet systems, the exposure of humans to ozone is considered detrimental.

OBJECTS OF THE INVENTION

It is an object of the invention to provide a method and apparatus for controlling microbial growth on condensation coil apparatus which is inexpensive, practical, may be utilized with air handling systems, and may be automatically operated without attention by the user.

Another object of the invention is to provide a method and apparatus for controlling microbial growth on condensation apparatus within air handling systems wherein a strong anti-microbial disinfectant is periodically applied to the apparatus surfaces upon which microorganisms may grow, and yet, the disinfectant is removed from the air handling system prior to restoration of the system to its normal operating cycle to prevent contamination of the system with the disinfectant.

Yet another object of the invention is to provide a method and apparatus for controlling microbial growth on the condensation apparatus of air handling systems wherein a strong disinfectant gas such as ozone may be temporarily introduced into the air handling system at the location of the condensation producing apparatus to treat the apparatus, and the ozone is then removed from the system prior to normal operation thereof.

SUMMARY OF THE INVENTION

In the practice of the invention an air handling system, such as an air conditioning or air cooling system, includes a chamber defined therein through which the air flows as produced by a primary air mover, such as a fan or blower. Moisture condensing apparatus, such as a heat exchanging coil, or the like, is located within the chamber wherein the temperature of air flowing therethrough is reduced. Such a reduction in air temperature will cause condensation of water vapor within the air and this condensate quickly accumulates on the cooling coils and usually falls to a drip pan located below the coil and drained away. However, due to residual moisture and the long periods of time that moisture exists on the condensation apparatus within the chamber microbial growth on such moist surfaces will occur creating the aforementioned problems.

With the invention, provision is made to temporarily terminate air flow through the air handling or cooling system, even during a cooling cycle, wherein the primary air mover, such as the air conditioner blower, is temporarily deenergized. Upon air flow through the chamber and condensing coil terminating, the chamber is sealed with respect to the remainder of the air handling system by baffles or valves. After the chamber is sealed from the air handling system an auxiliary air flow is introduced into the sealed chamber to produce an air flow through the condensing coil and over all of the apparatus within the chamber.

The auxiliary air flow is exhausted exteriorally of the air handling system, and the auxiliary air flow is used to carry a disinfectant, such as ozone, through the chamber for disinfecting and sterilizing the surfaces of the condensation apparatus, such as the heat exchanging coil, drip pan, and the like.

The ozone may be generated by an ozone generator located directly within the source for producing the auxiliary air flow through the chamber, and the auxiliary air flow is maintained for a duration of time sufficient to treat and sterilize the condensation apparatus located within the chamber. After a predetermined time of exposure of the ozone to the chamber, the ozone generation is terminated, and the auxiliary air flow through the chamber is continued until all of the ozone has been exhausted from the chamber. Thereafter, the air handling system primary air blower is re-energized and the cooling cycle continued as air flows through the chamber and cool condensation producing coil.

In the practice of the invention, sufficient disinfecting of the condensation producing apparatus can be achieved by spacing timed disinfecting cycles through a twenty-four hour air cooling operation in a manner that the time that the air cooling system will be deenergized for air cooling purposes is insufficient as to adversely affect the air cooling system in a noticeable manner.

Preferably, the sealing of the chamber and the exhausting of the chamber is accomplished by structure which is of simple fabrication, and yet is foolproof and dependable in operation. For instance, the sealing of the chamber with respect to the adjacent portions of the air handling system may be accomplished by pivoted baffles or vanes located within the air handling system ducts. By pivoting the baffles at their upper edges the weight of the baffles will cause the baffle to hang downwardly due to gravitational forces and thereby seal the duct and prevent air flow from the air handling system into the chamber. However, upon energizing of the primary air mover the air mover is of sufficient capacity and power to cause the baffles to swing to an open condition to permit air flow through the air handling system and chamber. However, the capacity and power of the auxiliary air mover system used during disinfecting of the condensation producing apparatus is insufficient to displace the gravity closed baffles, and the baffles will effectively seal the chamber with respect to the remainder of the air handling system during the disinfecting and sterilizing cycle.

Likewise, an air pressure sensitive exhausting system is used to exhaust the auxiliary air flow and ozone from the chamber during the disinfecting cycle in order to remove the ozone from the primary air handlung system. In this respect, the exhausting apparatus includes a valve which will be shifted to a closed condition during normal operation of the air handling system due to the greater air pressure within the system. However, upon deenergizing of the primary air mover the exhausting apparatus valve will, under gravitational forces, open and establish communication between the chamber and an ozone filter exterior or the air handling system to permit the air and ozone moved by the auxiliary air blower to be removed from the air handling system prior to energizing of the primary air mover.

The operation of the primary and auxiliary air movers, as well as the operation of the ozone generator, is determined by timers and conventional electrical control apparatus, and the operation of the method and apparatus of the invention can be automatically controlled without requiring attention by the user.

BRIEF DESCRIPTION OF THE DRAWINGS

The aforementioned objects and advantages of the invention will be appreciated from the following description and accompanying drawings wherein:

FIG. 3 is an elevational, schematic, sectional view similar to FIG. 1, illustrating the components in the positions occurring during the disinfecting and sterilization cycle as produced by the auxiliary air mover, FIG. 4 is a sectional, schematic top plan view of the auxiliary air flow apparatus and controls, FIG. 5 is an enlarged, elevational, diametrical view of the chamber exhaust conduit, illustrating the ball valve in the closed condition, and FIG. 6 is an elevational sectional view similar to FIG. 5 illustrating the ball valve in the chamber open or exhausting position.

DESCRIPTION OF THE PREFERRED EMBODIMENT

Figure 1:
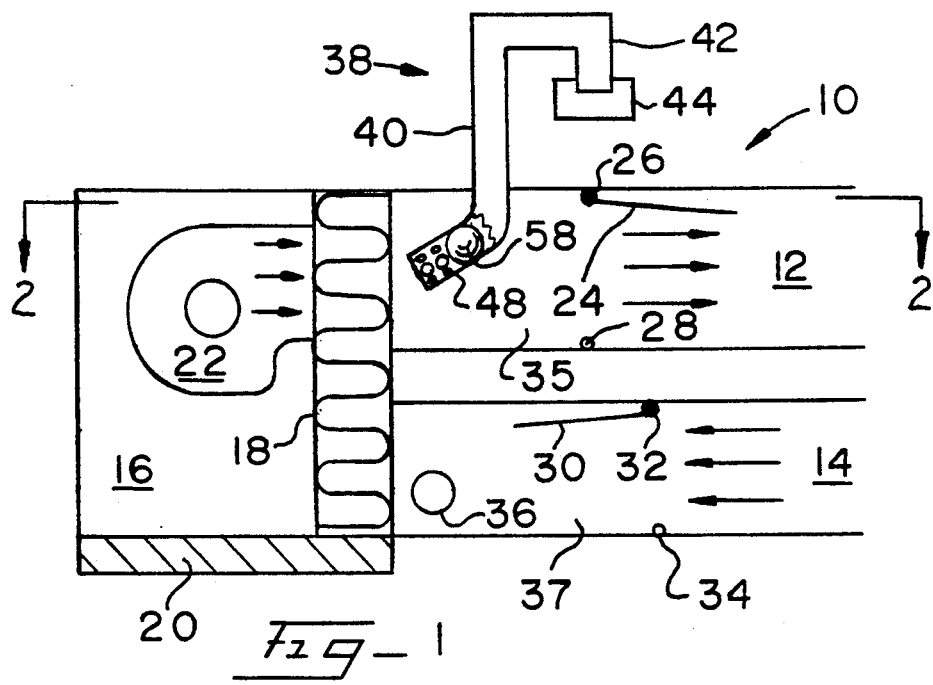
FIG. 1 is a schematic side elevational sectional view taken along Section 1—1 of FIG. 2 of an air handling system in accord with the invention illustrating the position of the components during normal operation.

In FIGS. 1—4 the air system 10 is illustrated in a generally schematic manner. In the illustrated version of the air system 10, the system includes an upper pressurized duct 12, a lower return air duct 14, and both of the ducts are in communication with a chamber 16. A heat exchanging coil 18, such as the evaporator coil of an air conditioning system, is located within the duct 16 and the coil 18 is connected to a refrigeration circuit, not shown, whereby refrigerant evaporating within the coil 18 cools the air flowing through the ducts 12 and 14 and chamber 16 condensing moisture upon the coil. A base 20, which may be in the form of a drip pan, is located below the coil 18 receiving moisture condensing thereon, and the base drip pan 20 normally includes a drain, not shown, whereby the majority of the moisture condensed upon coil 18 is drained away.

Figure 2:
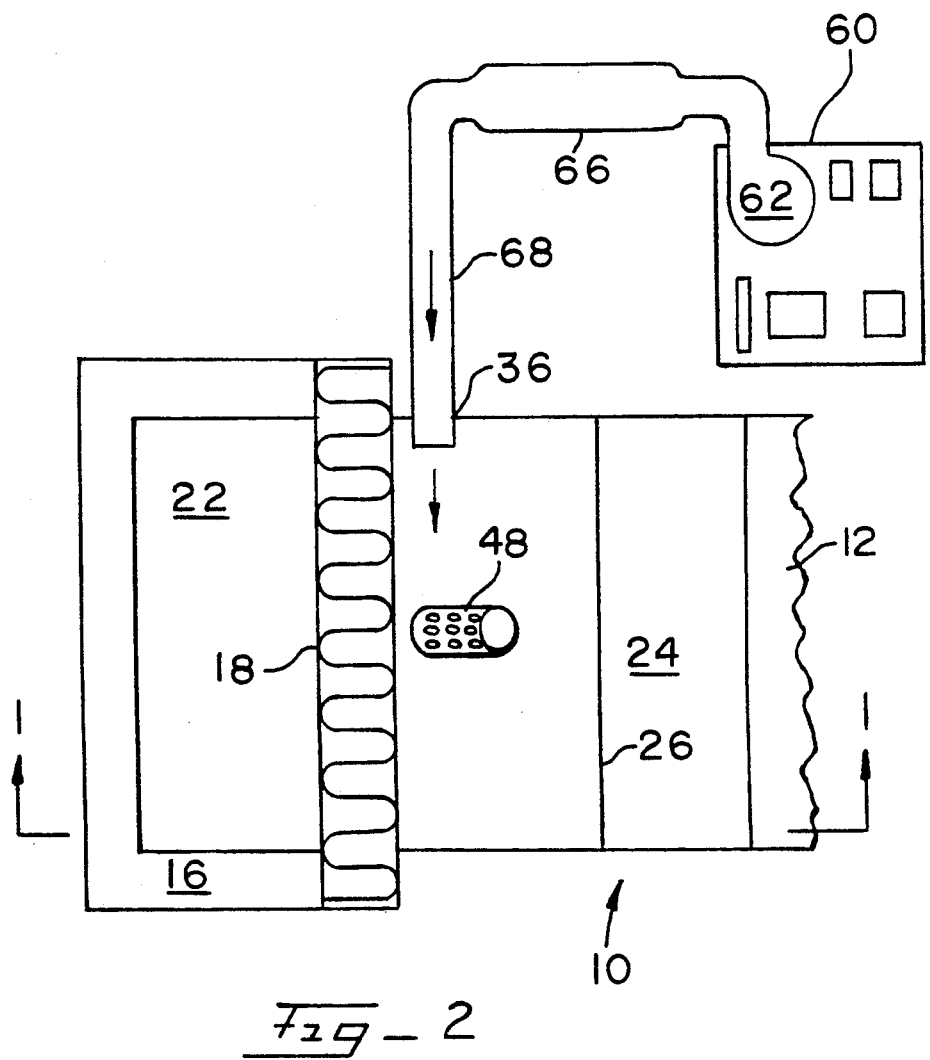
FIG. 2 is a schematic plan view of the apparatus of FIG. 1 as taken along Section 2—2 of FIG. 1, and illustrating the auxiliary air flow apparatus.

In FIGS. 1-3 the ducts 12 and 14 are illustrated in a parallel adjacent manner to each other, and the normal direction of air flow therethrough is indicated by the arrows, FIG. 1. It is also to be appreciated that the ducts 12 and 14 could be in opposed alignment each entering the chamber 16 from opposite directions. The particular arrangement of the chamber 16 to its associated ducts forms no part of the invention, but it is to be appreciated that all of the air flowing through the air system 10 will pass through the chamber 16 and the coil 18.

Air movement through the air system 10 is produced by the primary air mover 22 which comprises the typical squirrel cage fan or blower usually used with air conditioning systems. In the disclosed embodiment the primary air mover fan 22 is located within the chamber 16, but it is possible to locate the primary air mover elsewhere, such as in the return air duct 14, as is often the case.

A baffle 24 is located within the upper duct 12 and is pivotably mounted at its upper edge at 26. The baffle 24 is of sufficient vertical height as to seal the duct 12 when, under gravitational force, the baffle 24 is vertically oriented and engages the stop 28, FIG. 3.

In a similar manner, a baffle 30 is located within lower duct 14 and is pivotably mounted at its upper edge at 32, and when vertically oriented under gravitational forces the baffle 30 will engage the stop 34, as shown in FIG. 3.

The purpose of the baffles 24 and 30 is to seal the chamber 16 with respect to the remainder of the air system 10 when the baffles are vertically oriented as shown in FIG. 3. When the primary air mover 22 is energized, as shown in FIG. 1, the power and capacity of the air mover 22 is sufficient to pivot the baffles 24 and 30 to their normal or open conditions as shown in FIG. 1. However, upon the primary air mover 22 being deenergized the baffles 24 and 30 will due to their weight, pivot to the positions shown in FIG. 3.

For purpose of description the portion of the duct 12 between the baffle 24 and the chamber 16 is designated as the outlet 35 of the chamber 16, while the portion of the duct 14 between the baffle 30 and the chamber 16 is designated as the chamber inlet 37.

A hole 36 is formed in the duct 14 within the chamber inlet 37, for a purpose later described, and the chamber exhaust system 38 communicates with the chamber outlet 35.

The chamber exhaust system 38 includes an upper conduit 40 which includes a neck 42 communicating with an ozone filter 44 which contains activated charcoal and discharges into the atmosphere. The duct 12 is provided with a hole 46 through which the conduit 40 extends, and the portion of the exhaust 38 within the chamber outlet 35 includes an oblique conduit portion 48 disposed at approximately 45° to the horizontal.

The lower end of the portion 48 includes an annular ring 50 having a central port 52, and the portion 48 also includes an annular ring 54 inwardly spaced from ring 50 which defines a central port 55, FIG. 6. A lightweight spherical ball 58 of a diameter slightly less than the bore of the portion 48 is freely movable within the bore portion 48 between the rings 50 and 54 as will be appreciated from FIGS. 5 and 6.

The apparatus includes a control box 60 located exteriorly of the air system 10 and an auxiliary air mover fan 62 is located within box 60. The auxiliary air mover 62 may comprise a small squirrel cage blower fan having an outlet conduit at 64 which communicates with the manifold 66. The manifold 66 includes an outlet conduit 68 which extends through the hole 36 formed in the duct 14. In this manner the outlet conduit 68 communicates with the chamber inlet 37.

An ozone generator 70 is located within the manifold 66, and the ozone generator 70 may consist of either a high voltage discharge system or an ozone generating ultraviolet light system as known within the art. The manner in which the ozone is generated does not constitute an aspect of the instant invention.

The box 60 also includes an air conditioner control 76 which in conjunction with a timed relay 72 controls operation of the primary air mover 22 and the refrigeration compressor, not shown, as well as controlling the blower control 78 for the auxiliary air mover 62. A timer 74, electrically connected to the controls 76, 78 and 72 controls the timing of the cycles of the apparatus, as later described.

Under normal operating conditions calling for cool air, the control 76 will be operated by a thermostat, not shown, and as long as cool air is required the refrigeration circuit compressor will be energized to provide refrigerant to the coil 18. Simultaneously, the primary air mover 22 will be in operation, and the flow of air through the system 10 will be as indicated by the arrows in FIG. 1. Duct 12 functions as the outlet for the cool air, the duct 14 constitutes a return air duct, and the air flow produced by the primary air mover 22 will maintain the baffles 24 and 30 in their open conditions as shown in FIG. 1.

Because of the size and capacity of the primary air mover 22, the air velocity and air pressure within the chamber outlet 35 will be at its maximum, which will force the lightweight ball valve 58 against the ring 54 as shown in FIGS. 1 and 5, and as engagement of the ball 58 with the ring 54 seals the port 55, no cooled air enters the exhaust system 38, and the exhaust system 38 is automatically closed when the primary air mover 22 is energized.

Upon the passing of a predetermined timed interval as determined by timer 74, the refrigeration compressor and primary air mover 22 are deenergized, and the deenergization of primary air mover 22 permits the baffles 24 and 30 to pivot to their closed positions as shown in FIG. 3 sealing the chamber 16 and its outlet 35 and inlet 37 from the remainder of the air system 10.

Under the control of timer 74, the auxiliary air mover 62 is now energized along with the energizing of the ozone generator 70. This action causes an auxiliary air flow from air mover 62 into the chamber inlet 37 through conduit 68. As the auxiliary air flow path from air mover 62 includes ozone generator 70 the air flowing into the chamber inlet 37 contains ozone.

Upon deenergizing of the primary air mover 22 the pressure forces acting upon the exhaust ball valve 58 terminate, and the weight of the ball 58 permits the ball to roll to the lower position shown in FIG. 6 wherein the ball 58 engages ring 50 and seals port 52. Positioning of the ball 58 against the ring 50 establishes communication between the plurality of orifices 56 defined in the exhaust portion 48 with the conduit 40 and ozone filter 44. Thus, when the primary air mover 22 is deenergized the exhaust system 38 automatically communicates with the chamber outlet 35.

As the auxiliary air mover 62 forces the ozone laden air into the chamber inlet 37 the anti-microbial ozone-air gas mixture cannot pass into the duct 14 since the baffle 30 is closed and in engagement with the stop 34, FIG. 3. Accordingly, the ozone laden air forced into the chamber inlet 37 will pass into the chamber 16 and the moist coil 18 and drip pan 20 will be exposed to the ozone being forced into the chamber 16. The ozone laden air passing through the coil 18 enters the chamber outlet 35 and the exhaust system orifices 56 and passes through the ozone filter 44 into the atmosphere exteriorly of the air system 10. The ozone will not enter duct 12 as the baffle 24 is engaging stop 28, FIG. 3, and sealing the duct 12 from outlet 35.

When the auxiliary air mover 62 is energized it is to be appreciated that the air pressure produced in chamber 16 is substantially less than that produced by the primary air mover 22, and the weight of baffle 24 and the ball valve 58 is sufficient to prevent displacement by the auxiliary air flow during the disinfecting cycle.

As determined by timer 74, the auxiliary air mover 62 and ozone generator 70 will operate for approximately ten minutes. The ozone generator operation is terminated prior to the termination of the auxiliary air mover 62 in order that the auxiliary air mover may purge all of the ozone from the chamber 16 and its outlet 35 and inlet 37 prior to restoration of the normal operation of the air system 10. After the ozone has been purged from the chamber and its outlet and inlet, the timer 74 will deactivate the auxiliary air mover 62, and energize the refrigeration circuit compressor and primary air mover 22 to restore the air system 10 to its normal air cooling operation. Once the primary air mover 22 is energized the baffles 24 and 30 will automatically open as shown in FIG. 1, and the pressure on ball 58 through port 52 will displace ball 58 inwardly and the ball 58 will engage the ring 54 to seal the exhaust 38 from the atmosphere.

Approximately every eight hours of operation of the air system 10, the aforementioned disinfecting and sanitizing cycle will be energized for about ten minutes. As the ozone entering the chamber 16 will be exposed to any microorganisms within the chamber, within the outlet 35 or chamber inlet 37, or on the base and drip pan 20, the ozone will kill such microorganisms and prevent their growth. As the baffles 24 and 30 are gravity operated, as is the exhaust ball valve 58 the disinfecting and sanitizing cycle of the apparatus will be dependable and automatic, and the practice of the invention will prevent the growth of organisms in air handling systems.

It is to be appreciated that the apparatus described may be retrofitted into existing air cooling systems upon the installation of baffles 24 and 30, exhaust system 38, and the apparatus for introducing ozone into the chamber. It is within the scope of the invention to use other gaseous disinfectants than ozone, and the sealing of the coil chamber and construction of the exhaust system may vary from that disclosed, and other modifications to the inventive concepts may be apparent to those skilled in the art without departing from the spirit and scope of the invention.

We claim:

1. The method for controlling microbial growth on cooling coil apparatus located within an air cooling system, comprising the steps of: providing a system including a first inlet passage having a first flow responsive valve open during primary air flow operation, a second outlet passage having a second flow responsive valve open during primary air flow operation, a chamber interconnecting the first and second passages, disinfectant gas outlet in communication with the chamber adjacent the outlet passage having a flow controlled valve closed during primary air flow operation of the air cooling system, a disinfectant gas circuit having a fan and an outlet in communication with the chamber adjacent the inlet passage, cooling coil apparatus within the chamber and a primary air mover selectively forcing air through the passages, chamber and cooling coil apparatus upon demand for cooled air, energizing the primary air mover during an air cooling cycle during demand for cooled air, timing the duration of the cooling cycle and sensing a first predetermined duration thereof, deenergizing the primary air mover upon sensing of said first predetermined duration to close the valves of the first and second passages sealing the chamber with respect to the first and second passages and opening the disinfectant gas outlet valve, introducing an anti-microbial disinfectant gas into the sealed chamber through the disinfectant gas circuit outlet by energization of the fan to treat the cooling coil apparatus, removing the anti-microbial disinfectant gas from the sealed chamber and air cooling system through the disinfectant gas outlet, and unsealing the chamber with respect to the first and second passages by opening the first and second flow responsive valves by energizing the primary air mover to initiate another first predetermined duration of the cooling cycle.

2. The method for controlling microbial growth on cooling coil apparatus as in claim 1 wherein the step of introducing an anti-microbial disinfectant gas into the sealed chamber comprises introducing ozone into the sealed chamber.

3. The method for controlling microbial growth on cooling coil apparatus as in claim 1 wherein the introducing and removing of an anti-microbial gas with respect to the sealed chamber comprises the steps of:

(a) producing an auxiliary air flow through the sealed chamber and cooling coil apparatus by the fan introducing air into the chamber through the gas circuit outlet, (b) generating ozone within said auxiliary air flow to produce the anti-microbial gas, (c) terminating the generation of ozone after the anti-microbial treatment of the cooling coil apparatus by the generated ozone for a second predetermined duration, and (d) maintaining the auxiliary air flow through the sealed chamber and exhausting the auxiliary air flow from the air cooling system through the gas outlet until the ozone is substantially removed from the sealed chamber.

4. In an apparatus for controlling microbial growth on condensation coil apparatus located within an air cooling system having an air passage and a primary air mover for selectively forcing air through the passage, the condensation coil apparatus being located within the air passage, the improvement comprising, a chamber defined within the air passage having air pressure therein and having an air inlet and an air outlet, the condensation coil apparatus being located within said chamber, a first flow controlled valve selectively sealing said chamber outlet, a second flow control valve selectively sealing said chamber inlet, said valves opening during primary air flow operation of the primary air mover and automatically closing upon deenergization of the primary air mover, anti-microbial gas supply means in communication with said chamber, gas control means selectively regulating the flow of anti-microbial gas from said gas supply means to said chamber during deenergization of the primary air mover, said first and second valves sealing said chamber outlet and inlet with respect to the air passage during anti-microbial gas flow to said chamber, and gas exhausting means having an inlet in communication with said chamber air outlet and an outlet exterior of the air cooling system, said gas exhausting means selectively exhausting said anti-microbial gas from said chamber and the air cooling system during deenergization of the primary air blower.

5. Apparatus for controlling microbial growth on condensation coil apparatus as in claim 4, an auxiliary air mover in communication with said chamber producing an auxiliary air flow, control means controlling operation of said auxiliary air mover, said auxiliary air flow carrying said anti-microbial gas through said chamber and the condensing coil and said exhausting means during deenergization of the primary air mover.

6. Apparatus for controlling microbial growth on condensation coil apparatus as in claim 5, said anti-microbial gas supply means comprising an ozone generator located within said auxiliary air flow.

7. Apparatus for controlling microbial growth on condensation coil apparatus as in claim 4, said gas exhausting means including a movable normally open valve element exposed to the air passage within said chamber, a surface defined on said valve element exposed to the air pressure within said chamber whereby said element closes said gas exhausting means upon energizing of the primary air mover, and a biasing force imposed on said valve element sufficient to prevent movement of said valve element to a closed position when said anti-microbial gas is being supplied to said chamber.

8. Apparatus for controlling microbial growth on condensation coil apparatus as in claim 7, said gas exhausting means including a conduit within said chamber obliquely inclined to the horizontal, said valve element comprising a spherical ball within said conduit displaceable therein between a first position closing said gas exhausting means and a second position opening said gas exhausting means, said surface being defined on said ball and said biasing force comprising gravitational force acting upon said ball.

* * * * *